US008725239B2

(12) United States Patent
Liao

(10) Patent No.: US 8,725,239 B2
(45) Date of Patent: May 13, 2014

(54) IDENTIFYING SEIZURES USING HEART RATE DECREASE

(75) Inventor: Wangcai Liao, Houston, TX (US)

(73) Assignee: Cyberonics, Inc., Houston, TX (US)

(*) Notice: Subject to any disclaimer, the term of this patent is extended or adjusted under 35 U.S.C. 154(b) by 313 days.

(21) Appl. No.: 13/093,475

(22) Filed: Apr. 25, 2011

(65) Prior Publication Data

US 2012/0271181 A1    Oct. 25, 2012

(51) Int. Cl.
*A61B 5/04* (2006.01)

(52) U.S. Cl.
USPC ............................................. 600/509

(58) Field of Classification Search
USPC .................................. 600/509, 9.509
See application file for complete search history.

(56) References Cited

U.S. PATENT DOCUMENTS

| | | |
|---|---|---|
| 4,172,459 A | 10/1979 | Hepp |
| 4,197,856 A | 4/1980 | Northrop |
| 4,291,699 A | 9/1981 | Geddes et al. |
| 4,320,766 A | 3/1982 | Alihanka et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,062,169 A | 11/1991 | Kennedy et al. |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,194,847 A | 3/1993 | Taylor et al. |
| 5,203,326 A | 4/1993 | Collins |

(Continued)

FOREIGN PATENT DOCUMENTS

| | | |
|---|---|---|
| EP | 1145736 | 10/2001 |
| EP | 1486232 | 12/2004 |

(Continued)

OTHER PUBLICATIONS

O'Donovan, Cormac et al. "Computerized Seizures Detection Based on Heart Rate Changes", Epilepsia, vol. 36, Suppl. 4; p. 7, 1995 (1 page).

(Continued)

*Primary Examiner* — George Manuel
(74) *Attorney, Agent, or Firm* — Cyberonics, Inc.

(57) ABSTRACT

Methods and systems for detecting a seizure event, including receiving heart beat data versus time for a patient, detecting an increase in the heart rate of a patient from a baseline heart rate to an elevated heart rate, detecting a decrease in heart rate from the elevated heart rate, for a time interval occurring during said decrease in heart rate, determining at least one of a) a rate of decrease in heart rate and b) a rate of change in a rate of decrease in heart rate, and detecting a seizure event in response to determining at least one of a) a rate of decrease in heart rate greater than a threshold rate of decrease, and b) a rate of change in the rate of decrease less than a threshold rate of change in a rate of decrease.

20 Claims, 7 Drawing Sheets

(56) References Cited

U.S. PATENT DOCUMENTS

| | | | |
|---|---|---|---|
| 5,205,285 | A | 4/1993 | Baker, Jr. |
| 5,213,568 | A | 5/1993 | Lattin et al. |
| 5,215,086 | A | 6/1993 | Terry, Jr. et al. |
| 5,215,089 | A | 6/1993 | Baker, Jr. |
| 5,222,494 | A | 6/1993 | Baker, Jr. |
| 5,231,988 | A | 8/1993 | Wernicke et al. |
| 5,235,980 | A | 8/1993 | Varrichio et al. |
| 5,237,991 | A | 8/1993 | Baker, Jr. et al. |
| 5,243,980 | A | 9/1993 | Mehra |
| 5,251,634 | A | 10/1993 | Weinberg |
| 5,263,480 | A | 11/1993 | Wernicke et al. |
| 5,269,302 | A | 12/1993 | Swartz et al. |
| 5,269,303 | A | 12/1993 | Wernicke et al. |
| 5,299,569 | A | 4/1994 | Wernicke et al. |
| 5,304,206 | A | 4/1994 | Baker, Jr. et al. |
| 5,311,876 | A | 5/1994 | Olsen et al. |
| 5,313,953 | A | 5/1994 | Yomtov et al. |
| 5,330,507 | A | 7/1994 | Schwartz |
| 5,330,515 | A | 7/1994 | Rutecki et al. |
| 5,334,221 | A | 8/1994 | Bardy |
| 5,335,657 | A | 8/1994 | Terry, Jr. et al. |
| 5,404,877 | A | 4/1995 | Nolan et al. |
| 5,425,373 | A | 6/1995 | Causey, III |
| 5,513,649 | A | 5/1996 | Gevins et al. |
| 5,522,862 | A | 6/1996 | Testerman et al. |
| 5,523,742 | A | 6/1996 | Simkins et al. |
| 5,540,730 | A | 7/1996 | Terry, Jr. et al. |
| 5,540,734 | A | 7/1996 | Zabara |
| 5,571,150 | A | 11/1996 | Wernicke et al. |
| 5,610,590 | A | 3/1997 | Johnson et al. |
| 5,611,350 | A | 3/1997 | John |
| 5,645,077 | A | 7/1997 | Foxlin |
| 5,645,570 | A | 7/1997 | Corbucci |
| 5,651,378 | A | 7/1997 | Matheny et al. |
| 5,658,318 | A | 8/1997 | Stroetmann et al. |
| 5,683,422 | A | 11/1997 | Rise et al. |
| 5,690,681 | A | 11/1997 | Geddes et al. |
| 5,690,688 | A | 11/1997 | Noren et al. |
| 5,700,282 | A | 12/1997 | Zabara |
| 5,707,400 | A | 1/1998 | Terry, Jr. et al. |
| 5,716,377 | A | 2/1998 | Rise et al. |
| 5,720,771 | A | 2/1998 | Snell |
| 5,743,860 | A | 4/1998 | Hively et al. |
| 5,748,113 | A | 5/1998 | Torch |
| 5,792,186 | A | 8/1998 | Rise |
| 5,800,474 | A | 9/1998 | Benabid et al. |
| 5,807,284 | A | 9/1998 | Foxlin |
| 5,808,552 | A | 9/1998 | Wiley et al. |
| 5,833,709 | A | 11/1998 | Rise et al. |
| 5,853,005 | A | 12/1998 | Scanlon et al. |
| 5,871,517 | A * | 2/1999 | Abrams et al. .................. 607/45 |
| 5,879,309 | A | 3/1999 | Johnson et al. |
| 5,905,436 | A | 5/1999 | Dwight et al. |
| 5,913,876 | A | 6/1999 | Taylor et al. |
| 5,916,181 | A | 6/1999 | Socci et al. |
| 5,916,239 | A | 6/1999 | Geddes et al. |
| 5,928,272 | A * | 7/1999 | Adkins et al. .................. 607/45 |
| 5,941,906 | A | 8/1999 | Barreras, Sr. et al. |
| 5,942,979 | A | 8/1999 | Luppino |
| 5,978,702 | A | 11/1999 | Ward et al. |
| 5,978,972 | A | 11/1999 | Stewart et al. |
| 5,987,352 | A | 11/1999 | Klein et al. |
| 5,995,868 | A | 11/1999 | Osorio et al. |
| 6,016,449 | A | 1/2000 | Fischell et al. |
| 6,018,682 | A | 1/2000 | Rise |
| 6,048,324 | A | 4/2000 | Socci et al. |
| 6,061,593 | A | 5/2000 | Fischell et al. |
| 6,073,048 | A | 6/2000 | Kieval et al. |
| 6,083,249 | A | 7/2000 | Familoni |
| 6,091,992 | A | 7/2000 | Bourgeois et al. |
| 6,095,991 | A | 8/2000 | Krausman et al. |
| 6,104,956 | A | 8/2000 | Naritoku et al. |
| 6,115,628 | A | 9/2000 | Stadler et al. |
| 6,115,630 | A | 9/2000 | Stadler et al. |
| 6,128,538 | A | 10/2000 | Fischell et al. |
| 6,134,474 | A | 10/2000 | Fischell et al. |
| 6,162,191 | A | 12/2000 | Foxlin |
| 6,163,281 | A | 12/2000 | Torch |
| 6,167,311 | A | 12/2000 | Rezai |
| 6,171,239 | B1 | 1/2001 | Humphrey |
| 6,175,764 | B1 | 1/2001 | Loeb et al. |
| 6,205,359 | B1 | 3/2001 | Boveja |
| 6,208,894 | B1 | 3/2001 | Schulman et al. |
| 6,208,902 | B1 | 3/2001 | Boveja |
| 6,221,908 | B1 | 4/2001 | Kilgard et al. |
| 6,246,344 | B1 | 6/2001 | Torch |
| 6,248,080 | B1 | 6/2001 | Miesel et al. |
| 6,253,109 | B1 | 6/2001 | Gielen |
| 6,269,270 | B1 | 7/2001 | Boveja |
| 6,272,379 | B1 | 8/2001 | Fischell et al. |
| 6,304,775 | B1 | 10/2001 | Iasemidis et al. |
| 6,315,740 | B1 | 11/2001 | Singh |
| 6,324,421 | B1 | 11/2001 | Stadler et al. |
| 6,337,997 | B1 | 1/2002 | Rise |
| 6,339,725 | B1 | 1/2002 | Naritoku et al. |
| 6,341,236 | B1 | 1/2002 | Osorio et al. |
| 6,356,784 | B1 | 3/2002 | Lozano et al. |
| 6,356,788 | B2 | 3/2002 | Boveja |
| 6,361,507 | B1 | 3/2002 | Foxlin |
| 6,361,508 | B1 | 3/2002 | Johnson et al. |
| 6,366,813 | B1 | 4/2002 | DiLorenzo |
| 6,366,814 | B1 | 4/2002 | Boveja |
| 6,374,140 | B1 | 4/2002 | Rise |
| 6,397,100 | B2 | 5/2002 | Stadler et al. |
| 6,427,086 | B1 | 7/2002 | Fischell et al. |
| 6,429,217 | B1 | 8/2002 | Puskas |
| 6,441,731 | B1 | 8/2002 | Hess |
| 6,449,512 | B1 | 9/2002 | Boveja |
| 6,459,936 | B2 | 10/2002 | Fischell et al. |
| 6,463,328 | B1 | 10/2002 | John |
| 6,466,822 | B1 | 10/2002 | Pless |
| 6,473,639 | B1 | 10/2002 | Fischell et al. |
| 6,473,644 | B1 | 10/2002 | Terry, Jr. et al. |
| 6,477,418 | B2 | 11/2002 | Plicchi et al. |
| 6,480,743 | B1 | 11/2002 | Kirkpatrick et al. |
| 6,484,132 | B1 | 11/2002 | Hively et al. |
| 6,501,983 | B1 | 12/2002 | Natarajan et al. |
| 6,505,074 | B2 | 1/2003 | Boveja et al. |
| 6,532,388 | B1 | 3/2003 | Hill et al. |
| 6,539,263 | B1 | 3/2003 | Schiff et al. |
| 6,542,081 | B2 | 4/2003 | Torch |
| 6,542,774 | B2 | 4/2003 | Hill et al. |
| 6,549,804 | B1 | 4/2003 | Osorio et al. |
| 6,556,868 | B2 | 4/2003 | Naritoku et al. |
| 6,560,486 | B1 | 5/2003 | Osorio et al. |
| 6,564,102 | B1 | 5/2003 | Boveja |
| 6,587,719 | B1 | 7/2003 | Barrett et al. |
| 6,587,727 | B2 | 7/2003 | Osorio et al. |
| 6,594,524 | B2 | 7/2003 | Esteller et al. |
| 6,599,250 | B2 | 7/2003 | Webb et al. |
| 6,609,025 | B2 | 8/2003 | Barrett et al. |
| 6,610,713 | B2 | 8/2003 | Tracey |
| 6,611,715 | B1 | 8/2003 | Boveja |
| 6,611,783 | B2 | 8/2003 | Kelly, Jr. et al. |
| 6,615,081 | B1 | 9/2003 | Boveja |
| 6,615,085 | B1 | 9/2003 | Boveja |
| 6,622,038 | B2 | 9/2003 | Barrett et al. |
| 6,622,041 | B2 | 9/2003 | Terry, Jr. et al. |
| 6,622,047 | B2 | 9/2003 | Barrett et al. |
| 6,628,985 | B2 | 9/2003 | Sweeney et al. |
| 6,628,987 | B1 | 9/2003 | Hill et al. |
| 6,629,990 | B2 | 10/2003 | Putz et al. |
| 6,647,296 | B2 | 11/2003 | Fischell et al. |
| 6,656,125 | B2 | 12/2003 | Misczynski et al. |
| 6,656,960 | B2 | 12/2003 | Puskas |
| 6,668,191 | B1 | 12/2003 | Boveja |
| 6,671,555 | B2 | 12/2003 | Gielen et al. |
| 6,671,556 | B2 | 12/2003 | Osorio et al. |
| 6,684,105 | B2 | 1/2004 | Cohen et al. |
| 6,721,603 | B2 | 4/2004 | Zabara et al. |
| 6,730,047 | B2 | 5/2004 | Socci et al. |
| 6,735,474 | B1 | 5/2004 | Loeb et al. |
| 6,738,671 | B2 | 5/2004 | Christophersom et al. |
| 6,760,626 | B1 | 7/2004 | Boveja |

(56) References Cited

U.S. PATENT DOCUMENTS

| | | |
|---|---|---|
| 6,763,256 B2 | 7/2004 | Kimball et al. |
| 6,768,969 B1 | 7/2004 | Nikitin et al. |
| 6,786,877 B2 | 9/2004 | Foxlin |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,850,601 B2 | 2/2005 | Jones et al. |
| 6,879,850 B2 | 4/2005 | Kimball |
| 6,885,888 B2 | 4/2005 | Rezai |
| 6,904,390 B2 | 6/2005 | Nikitin et al. |
| 6,920,357 B2 | 7/2005 | Osorio et al. |
| 6,923,784 B2 | 8/2005 | Stein |
| 6,931,274 B2 | 8/2005 | Williams et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,984,993 B2 | 1/2006 | Ariav |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,035,684 B2 | 4/2006 | Lee |
| 7,054,792 B2 | 5/2006 | Frei et al. |
| 7,058,453 B2 | 6/2006 | Nelson et al. |
| 7,068,842 B2 | 6/2006 | Liang et al. |
| 7,076,288 B2 | 7/2006 | Skinner |
| 7,077,810 B2 | 7/2006 | Lange et al. |
| 7,079,977 B2 | 7/2006 | Osorio et al. |
| 7,104,947 B2 | 9/2006 | Riehl et al. |
| 7,110,820 B2 | 9/2006 | Tcheng et al. |
| 7,112,319 B2 | 9/2006 | Broderick et al. |
| 7,127,370 B2 | 10/2006 | Kelly et al. |
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| RE39,539 E | 4/2007 | Torch |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,274,298 B2 | 9/2007 | Frank |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,304,580 B2 | 12/2007 | Sullivan et al. |
| 7,305,268 B2 | 12/2007 | Gliner et al. |
| 7,313,440 B2 | 12/2007 | Miesel |
| 7,314,451 B2 | 1/2008 | Halperin et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,330,760 B2 | 2/2008 | Heruth et al. |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,385,443 B1 | 6/2008 | Denison |
| 7,389,144 B1 | 6/2008 | Osorio et al. |
| 7,389,147 B2 | 6/2008 | Wahlstrand et al. |
| 7,395,113 B2 | 7/2008 | Heruth et al. |
| 7,401,008 B2 | 7/2008 | Frei et al. |
| 7,403,820 B2 | 7/2008 | DiLorenzo |
| 7,420,472 B2 | 9/2008 | Tran |
| 7,433,732 B1 | 10/2008 | Carney et al. |
| 7,447,545 B2 | 11/2008 | Heruth et al. |
| 7,454,245 B2 | 11/2008 | Armstrong et al. |
| 7,488,293 B2 | 2/2009 | Marcovecchio et al. |
| 7,488,294 B2 | 2/2009 | Torch |
| 7,491,181 B2 | 2/2009 | Heruth et al. |
| 7,494,464 B2 | 2/2009 | Rzesnitzek et al. |
| 7,502,643 B2 | 3/2009 | Farringdon et al. |
| 7,515,054 B2 | 4/2009 | Torch |
| 7,539,532 B2 | 5/2009 | Tran |
| 7,539,533 B2 | 5/2009 | Tran |
| 7,539,543 B2 | 5/2009 | Schiff et al. |
| 7,558,622 B2 | 7/2009 | Tran |
| 7,565,132 B2 | 7/2009 | Ben |
| 7,590,453 B2 | 9/2009 | Heruth et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,658,112 B2 | 2/2010 | Nakamura |
| 7,666,151 B2 | 2/2010 | Sullivan et al. |
| 7,714,757 B2 | 5/2010 | Denison et al. |
| 7,717,848 B2 | 5/2010 | Heruth et al. |
| RE41,376 E | 6/2010 | Torch |
| 7,733,224 B2 | 6/2010 | Tran |
| 7,747,318 B2 | 6/2010 | John et al. |
| 7,769,464 B2 | 8/2010 | Gerber et al. |
| 7,775,993 B2 | 8/2010 | Heruth et al. |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,813,802 B2 | 10/2010 | Tcheng et al. |
| 7,822,481 B2 | 10/2010 | Gerber et al. |
| 7,827,011 B2 | 11/2010 | DeVaul et al. |
| 7,831,305 B2 | 11/2010 | Gliner |
| 7,847,628 B2 | 12/2010 | Denison |
| 7,866,212 B2 | 1/2011 | Ariav et al. |
| 7,899,545 B2 | 3/2011 | John |
| 7,935,076 B2 | 5/2011 | Estes et al. |
| RE42,471 E | 6/2011 | Torch |
| 7,957,809 B2 | 6/2011 | Bourget et al. |
| 7,965,833 B2 | 6/2011 | Meir et al. |
| 7,974,671 B2 | 7/2011 | Fujiwara et al. |
| 7,996,076 B2 | 8/2011 | Burns et al. |
| 7,999,857 B2 | 8/2011 | Bunn et al. |
| 8,000,789 B2 | 8/2011 | Denison et al. |
| 8,000,794 B2 | 8/2011 | Lozano |
| 8,021,299 B2 | 9/2011 | Miesel et al. |
| 8,027,730 B2 | 9/2011 | John et al. |
| 8,027,737 B2 | 9/2011 | Kokones et al. |
| 8,075,499 B2 | 12/2011 | Nathan et al. |
| 8,109,891 B2 | 2/2012 | Kramer et al. |
| 2001/0032059 A1 | 10/2001 | Kelly et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0040680 A1 | 2/2003 | Hassert et al. |
| 2003/0074032 A1 | 4/2003 | Gliner |
| 2003/0083716 A1 | 5/2003 | Nicolelis et al. |

(56) References Cited

U.S. PATENT DOCUMENTS

| | | |
|---|---|---|
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0195588 A1 | 10/2003 | Upton et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236474 A1 | 12/2003 | Singh |
| 2003/0236558 A1 | 12/2003 | Whitehurst et al. |
| 2004/0006278 A1 | 1/2004 | Webb et al. |
| 2004/0030365 A1 | 2/2004 | Rubin et al. |
| 2004/0088024 A1 | 5/2004 | Firlik et al. |
| 2004/0111045 A1 | 6/2004 | Sullivan et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0225335 A1 | 11/2004 | Whitehurst et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0022606 A1 | 2/2005 | Partin et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060001 A1 | 3/2005 | Singhal et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0107716 A1 | 5/2005 | Eaton et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0203366 A1 | 9/2005 | Donoghue et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0018833 A1 | 1/2006 | Murphy et al. |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0149139 A1 | 7/2006 | Bonmassar et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0212097 A1 | 9/2006 | Varadan et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | Dilorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | Dilorenzo |
| 2007/0142873 A1 | 6/2007 | Esteller et al. |
| 2007/0150024 A1 | 6/2007 | Leyde et al. |
| 2007/0150025 A1 | 6/2007 | Dilorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0242661 A1 | 10/2007 | Tran et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0004904 A1 | 1/2008 | Tran et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |

(56) References Cited

U.S. PATENT DOCUMENTS

| | | |
|---|---|---|
| 2008/0071323 A1 | 3/2008 | Lowry et al. |
| 2008/0077028 A1 | 3/2008 | Schaldach et al. |
| 2008/0081958 A1 | 4/2008 | Denison et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0208013 A1 | 8/2008 | Zhang et al. |
| 2008/0208284 A1 | 8/2008 | Rezai et al. |
| 2008/0258907 A1 | 10/2008 | Kalpaxis |
| 2008/0269579 A1 | 10/2008 | Schiebler et al. |
| 2008/0275327 A1 | 11/2008 | Faarbaek et al. |
| 2008/0275328 A1 | 11/2008 | Jones et al. |
| 2008/0275349 A1 | 11/2008 | Halperin et al. |
| 2008/0281376 A1 | 11/2008 | Gerber et al. |
| 2008/0281381 A1 | 11/2008 | Gerber et al. |
| 2008/0281550 A1 | 11/2008 | Hogle et al. |
| 2008/0319281 A1 | 12/2008 | Aarts et al. |
| 2009/0030345 A1 | 1/2009 | Bonnet et al. |
| 2009/0040052 A1 | 2/2009 | Cameron et al. |
| 2009/0054737 A1 | 2/2009 | Magar et al. |
| 2009/0054742 A1 | 2/2009 | Kaminska et al. |
| 2009/0060287 A1 | 3/2009 | Hyde et al. |
| 2009/0076350 A1 | 3/2009 | Bly et al. |
| 2009/0099624 A1 | 4/2009 | Kokones et al. |
| 2009/0099627 A1 | 4/2009 | Molnar et al. |
| 2009/0105785 A1 | 4/2009 | Wei et al. |
| 2009/0137921 A1 | 5/2009 | Kramer et al. |
| 2009/0227882 A1 | 9/2009 | Foo |
| 2009/0227888 A1 | 9/2009 | Salmi |
| 2009/0322540 A1 | 12/2009 | Richardson et al. |
| 2010/0010382 A1 | 1/2010 | Panken |
| 2010/0010392 A1 | 1/2010 | Skelton et al. |
| 2010/0010583 A1 | 1/2010 | Panken et al. |
| 2010/0023348 A1 | 1/2010 | Hardee et al. |
| 2010/0056878 A1 | 3/2010 | Partin et al. |
| 2010/0106217 A1 | 4/2010 | Colborn |
| 2010/0109875 A1 | 5/2010 | Ayon et al. |
| 2010/0121214 A1 | 5/2010 | Giftakis et al. |
| 2010/0217533 A1 | 8/2010 | Nadkarni et al. |
| 2010/0223020 A1 | 9/2010 | Goetz |
| 2010/0228103 A1 | 9/2010 | Schecter |
| 2010/0228314 A1 | 9/2010 | Goetz |
| 2010/0268056 A1 | 10/2010 | Picard et al. |
| 2010/0280336 A1 | 11/2010 | Giftakis et al. |
| 2010/0280578 A1 | 11/2010 | Skelton et al. |
| 2010/0280579 A1 | 11/2010 | Denison et al. |
| 2010/0286567 A1 | 11/2010 | Wolfe et al. |
| 2010/0298661 A1 | 11/2010 | McCombie et al. |
| 2010/0298742 A1 | 11/2010 | Perlman et al. |
| 2010/0305665 A1 | 12/2010 | Miesel et al. |
| 2010/0312188 A1 | 12/2010 | Robertson et al. |
| 2011/0029044 A1 | 2/2011 | Hyde et al. |
| 2011/0040204 A1 | 2/2011 | Ivorra et al. |
| 2011/0040546 A1 | 2/2011 | Gerber et al. |
| 2011/0060252 A1 | 3/2011 | Simonsen et al. |
| 2011/0066062 A1 | 3/2011 | Banet et al. |
| 2011/0066081 A1 | 3/2011 | Goto et al. |
| 2011/0137372 A1 | 6/2011 | Makous et al. |
| 2011/0172545 A1 | 7/2011 | Grudic et al. |
| 2011/0230730 A1 | 9/2011 | Quigg et al. |
| 2011/0245629 A1 | 10/2011 | Giftakis et al. |
| 2011/0251469 A1 | 10/2011 | Varadan |
| 2011/0270117 A1 | 11/2011 | Warwick et al. |
| 2011/0270134 A1 | 11/2011 | Skelton et al. |
| 2011/0295127 A1 | 12/2011 | Sandler et al. |
| 2011/0306846 A1 | 12/2011 | Osorio |
| 2011/0313484 A1 | 12/2011 | Hincapie et al. |

FOREIGN PATENT DOCUMENTS

| | | |
|---|---|---|
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

Robinson, Stephen E. et al. "Heart Rate Variability Changes as Predictor of Response to Vagal Nerve Stimulation Therapy for Epilepsy", Epilepsia, vol. 40, Suppl. 7, p. 147; 1999 (1 page).

Long, Teresa J. et al. "Effectiveness of Heart Rate Seizures Detection Compared to EEG in an Epilepsy Monitoring Unit (EMU)", Epilepsia, vol. 40, Suppl. 7, p. 174; 1999 (1 page).

Dimkpa, Uchechukwu "Post-Exercise Heart Rate Recovery; An Index of Cardiovascular Fitness", Official Research Journal of the American Society of Exercise Physiologists (ASEP), vol. 12, No. 1, pp. 10-23, Feb. 2009 (14 pages).

Hautala, Arto J. et al. "Heart Rate Recovery After Maximal Exercise is Associated with Acetylcholine Receptor M2 (CHRM2) Gene Polymorphism", American Journal Physiological Society, Circ Physiol 291, pp. H459-H466, Feb. 26, 2006 (8 pages).

Nishime, Erna Obenza et al. "Heart Rate Recovery and Treadmill Exercise Score as Predictors of Mortality in Patients Referred for Exercise ECG", Journal of American Medical Association, vol. 284, No. 11, pp. 1392-1398, Sep. 20, 2000 (7 pages).

Du, Na et al. "Heart Rate Recovery After Exercise and Neural Regulation of Heart Rate Variability in 30-40 Year Old Female Marathon Runners", Journal of Sports and Medicine, pp. 9-17, 2005, (9 pages).

International Search Report and Written Opinion received in corresponding PCT Application No. PCT/US2011/061624 from the International Searching Authority dated Feb. 1, 2012, 13 pages.

Van Elmpt, Wouter J.C. et al.; "A Model of Heart Rate Changes to Detect Seizures in Severe Epilepsy"; Seizure, Bailliere Tindall, London, GB; vol. 15, No. 6; Sep. 1, 2006; pp. 366-375.

Smith, P.E.M. et al.; "Profiles of Instant Heart Rate During Partial Seizures"; Electroencephalography and Clinical Neurophysiology, Elsevier; vol. 72, No. 3, Mar. 1, 1989, pp. 207-217.

Bachman, D.,S. et al.; "*Effects of Vagal Volleys and Serotonin on Units of Cingulate Cortex in Monkeys;*" Brain Research, vol. 130 (1977). pp. 253-269.

Baevskii, R.M. "*Analysis of Heart Rate Variability in Space Medicine;*" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station;*" J. Applied Physiological, vol. 103, (2007) pp. 156-161.

Boon, P., et al.; "*Vagus Nerve Stimulation for Epilepsy, Clinical Efficacy of Programmed and Magnet Stimulation;*" (2001); pp. 93-98.

Boon, Paul, et al.; "*Programmed and Magnet-Induced Vagus Nerve Stimulation for Refractory Epilepsy;*" Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin;*" Letters to Nature; vol. 405; (May 2000); pp. 458-462.

(56) References Cited

OTHER PUBLICATIONS

Brack, Kieran E., et al.; "*Interaction Between Direct Sympathetic and Vagus Nerve Stimulation on Heart Rate in the Isolated Rabbit Heart;*" Experimental Physiology vol. 89, No. 1; pp. 128-139.

Chakravarthy, N., et al.; "*Controlling Synchronization in a Neuron-Level Population Model;*" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat;*" Neurobiology of Learning and Memory, vol. 70, 364-373 (1998) Art. No. NL983863.

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and on Its Variability in Humans:*" Epilepsia, vol. 42, No. 8 (2001); pp. 1007-1016.

George, M.S., et al.; "*Vagus Nerve Stimulation: A New Tool for Brain Research and Therapy;*" Society of Biological Psychiatry vol. 47 (2000) pp. 287-295.

"*Heart Rate Variability—Standards of Measurement, Physiological Interpretation, and Clinical Use*" Circulation-Electrophysiology vol. 93, No. 5; http://circ.ahajournals.org/cgi/content-nw/full/93/5/1043/F3.

Henry, Thomas R.; "*Therapeutic Mechanisms of Vague Name Stimulation;*". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys;*" Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques;*" IEEE Transactions on Biomedical Engineering, vol. 51, No. 3 (Mar. 2004); pp. 493-506.

Iasemidis; L.D., et al.; "*Spatiotemporal Transition to Epileptic Seizures: A Nonlinear Dynamical Analysis of Scalp and Intracranial EEG Recordings;*"Spatiotemporal Models in Biological and Artificial Systems; F.L. Silva et al. (Eds.) IOS Press, 1997; pp. 81-88.

Iasemidis, L.D.; "Epileptic Seizure Prediction and Control" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*"Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press—YSEIZ—1305; pp. 1-4.

Koo, B., "*EEG Changes With Vagus Nerve Stimulation*" Journal of Clinical Neurophysiology, vol. 18 No. 5 (Sep. 2001); pp. 434-441.

Krittayaphong, M.D., et al.; "*Heart Rate Variability in Patients with Coronary Artery Disease: Differences in Patients with Higher and Lower Depression Scores*" Psychosomatic Medicine vol. 59 (1997) pp. 231-235.

Leutmezer, F., et al.; "*Electrocardiographic Changes at the Onset of Epileptic Seizures;*" Epilepsia, vol. 44, No. 3; (2003); pp. 348-354.

Lewis, M.E., et al.; "*Vagus Nerve Stimulation Decreases Left Ventricular Contractility in Vivo in the Human and Pig Heart*" The Journal of Physiology vol. 534, No. 2, (2001) pp. 547-552.

Li, M., et al.; "*Vagal Nerve Stimulation Markedly Improves Long-Term Survival After Chronic Heart Failure in Rats;*" Circulation (Jan. 2004) pp. 120-124.

Licht, C.M.M.; *Association Between Major Depressive Disorder and Heart Rate Variability in the Netherlands Study of Depression and Anxiety (NESDA)*; Arch. Gen Psychiatry, vol. 65, No. 12 (Dec. 2008); pp. 1358-1367.

Lockard et al., "*Feasibility and Safety of Vagal Stimulation in Monkey Model;*" Epilepsia, vol. 31 (Supp. 2) (1990), pp. S20-S26.

McClintock, P., "*Can Noise Actually Boost Brain Power*" Physics World Jul. 2002; pp. 20-21.

Mori, T., et al.; "*Noise-Induced Entrainment and Stochastic Resonance in Human Brain Waves*" Physical Review Letters vol. 88, No. 21 (2002); pp. 218101-1-218101-4.

Mormann, F., "Seizure prediction: the long and winding road," Brain 130 (2007), 314-333.

Nouri, M.D.; "*Epilepsy and the Autonomic Nervous System*" emedicine (updated May 5, 2006); pp. 1-14; http://www.emedicine.com/neuro/topic658.htm.

O'Regan, M.E., et al.; "*Abnormalities in Cardiac and Respiratory Function Observed During Seizures in Childhood*" Developmental Medicine & Child Neurlogy, vol. 47 (2005) pp; 4-9.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "*Complex Estimation of Adaptation Abilities of the Organism in Children Using the Indices of Responsiveness of the Cardiovascular System and Characteristics of EEG*" Neurophysiology vol. 38, No. 1 (2006); pp. 63-74.

Rugg-Gunn, F.J., et al.; "*Cardiac Arrhythmias in Focal Epilepsy: a Prospective Long-Term Study*" www.thelancet.com vol. 364 (2004) pp. 2212-2219.

Sajadieh, a., et al.; "*Increased Heart Rate and Reduced Heart-Rte Variability are Associated with Subclinical Inflammation in Middle-Aged and Elderly Subjects with no. Apparent Heart Disease*" European Heart Journal vol. 25, (2004); pp. 363-370.

Schernthaner, C., et al.; "*Autonomic Epilepsy—The Influence of Epileptic Discharges on Heart Rate and Rhythm*"The Middle European Journal of Medicine vol. 111, No. 10 (1999) pp. 392-401.

Terry et al.; "*The Implantable Neurocybernetic Prosthesis System*", Pacing and Clinical Electrophysiology, vol. 14, No. 1 (Jan. 1991), pp. 86-93.

Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.

Umetani, M.D., et al.; "*Twenty-Four Hour Time Domain Heart Rate Variability and Heart Rate: Relations to Age and Gender Over Nince Decades*"JACC vol. 31, No. 3; (Mar. 1998); pp. 593-601.

Vonck, K., et al. "*The Mechanism of Action of Vagus Nerve Stimulation for Refractory Epilepsy—The Current Status*", Journal of Neurophysiology, vol. 18 No. 5 (2001), pp. 394-401.

Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.

Zabara, J.; "*Neuroinhibition of Xylaine Induced Emesis*" Pharmacology & Toxicology, vol. 63 (1988) pp. 70-74.

Zabara, J. "*Inhibition of Experimental Seizures in Canines by Repetivie Vagal Stimulation*" Epilepsia vol. 33, No. 6 (1992); pp. 1005-1012.

Zabara, J., et al.; "*Neural Control of Circulation I*"The Physiologist, vol. 28 No. 4 (1985); 1 page.

Zabara, J., et al.; "*Neuroinhibition in the Regulation of Emesis*" Space Life Sciences, vol. 3 (1972) pp. 282-292.

Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.

Osorio, Ivan et al., "Automated Seizure Abatement in Humans Using Electrical Stimulation," Annals of Neurology, vol. 57, No. 2, pp. 258-268, 2005.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Weil, Sabine et al, "Heart Rate Increase in Otherwise Subclinical Seizures Is Different in Temporal Versus Extratemporal Seizure Onset: Support for Temporal Lobe Automatic Influence," Epileptic Disord., vol. 7, No. 3, Sep. 2005, pp. 199-204.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

(56) References Cited

OTHER PUBLICATIONS

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

O'Donovan, Cormac a. et al., "Computerized Seizure Detection Based on Heart Rate Changes," abstract of AES Proceedings, Epilepsia, vol. 36, Suppl. 4, 1995, p. 7.

Robinson, Stephen E et al., "Heart Rate Variability Changes As Predictor of Response to Vagal Nerve Stimulation Therapy for Epilepsy," abstract of AES Proceedings, Epilepsia, vol. 40, Suppl. 7, 1999, p. 147.

Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

* cited by examiner

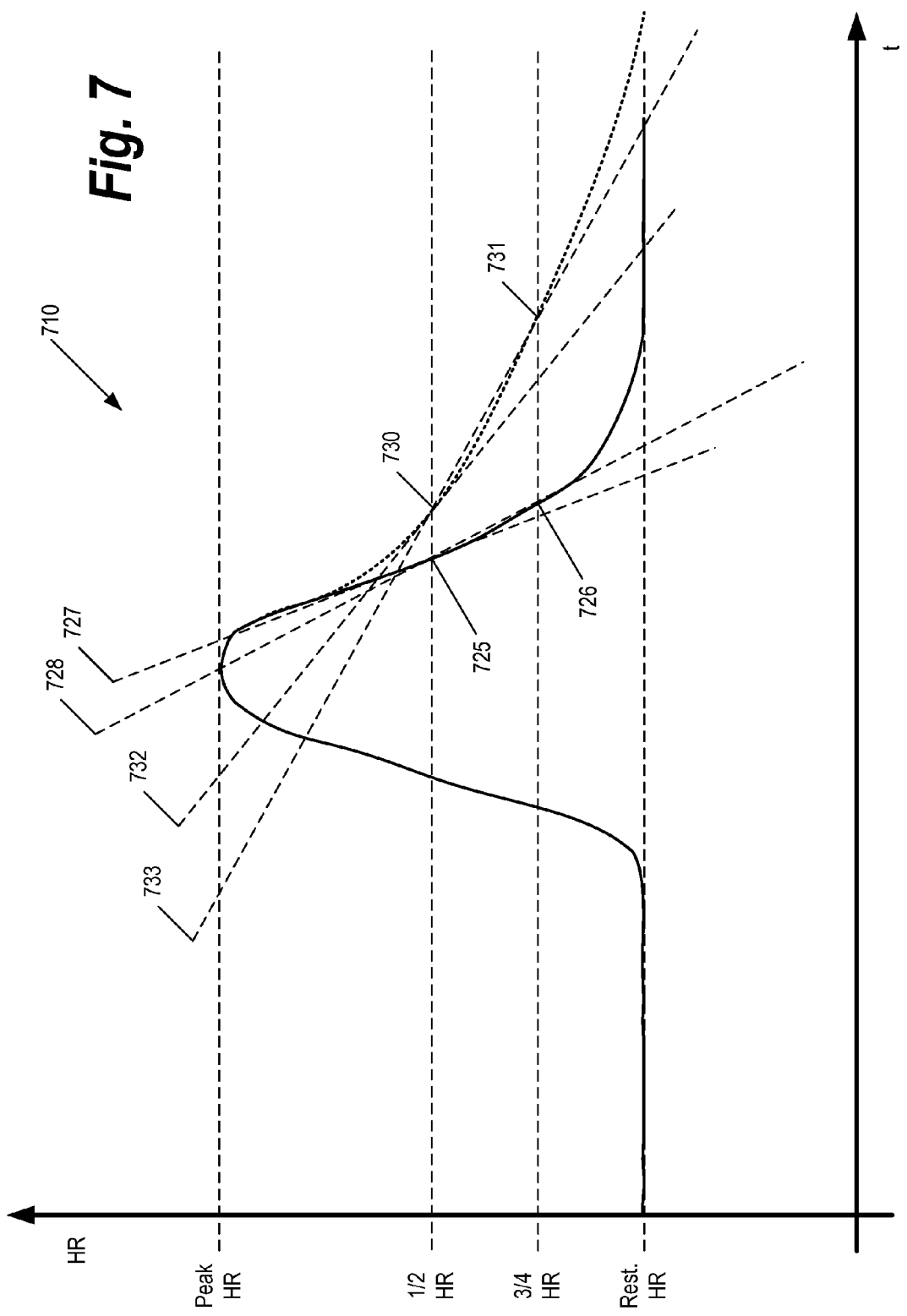

IDENTIFYING SEIZURES USING HEART RATE DECREASE

A. CROSS-REFERENCE TO RELATED APPLICATIONS

This application relates to the following commonly assigned co-pending application entitled:

"Identifying Seizures Using Heart Data From Two or More Windows" U.S. patent application 13/093,613, filed Apr. 25, 2011, Reference No. 100.235.

B. BACKGROUND

1. Technical Field of the Present Disclosure

The present disclosure relates generally to the field of seizure identification and more particularly to the field of identifying seizures by monitoring changes in heart rates.

2. Background of the Present Disclosure

Seizures are characterized by abnormal or excessive neural activity in the brain. Seizures may involve loss of consciousness or awareness, and result in falls, uncontrollable convulsions, etc. Significant injuries may result not only from the neuronal activity in the brain but also from the associated loss of motor function from falls or the inability of the patient to perceive and/or respond appropriately to potential danger or harm.

It is desirable to identify a seizure event as quickly as possible after the beginning of the seizure, to allow appropriate responsive action to be taken. Such actions may include sending an alert signal to the patient or a caregiver, taking remedial action such as making the patient and/or the immediate environment safe (e.g., terminating operation of equipment, sitting or lying down, moving away from known hazards), initiating a treatment therapy, etc. Where rapid detection is not possible or feasible, it is still desirable to be able to identify seizures after they have begun to allow a physician and/or caregiver to assess the patient's condition and determine whether existing therapies are effective or require modification and/or additional therapy modalities (for example, changing or adding additional drug therapies or adding a neurostimulation therapy). Seizure detection algorithms have been proposed using a variety of body parameters, including brain waves (e.g., electroencephalogram or EEG signals), heart beats (e.g., electrocardiogram or EKG), and movements (e.g., triaxial accelerometer signals). See, e.g., U.S. Pat. No. 5,928,272 and U.S. application Ser. No. 12/770,562, both of which are hereby incorporated by reference herein.

Detection of seizures using heart data requires that the seizure detection algorithm distinguish—or attempt to distinguish—between pathological changes in the detected heart signal (which may indicate a seizure) and non-pathological changes that may be similar to pathological changes but involve normal physiological functioning. For example, the patient's heart rate may increase both when a seizure event occurs and when the patient exercises, climbs stairs or performs other physiologically demanding acts. In some instances, state changes such as rising from a prone or sitting position to a standing position, such as in rising after a sleep period, may produce cardiac changes similar to seizure events. Thus, seizure detection algorithms must distinguish between changes in heart rate due to a seizure and those due to exertional or positional/postural changes.

Current algorithms fail to provide rapid and accurate detection. There is a need for improved algorithms that can more accurately distinguish between ictal and non-ictal heart rate changes. There is also a need for algorithms that may provide an initial detection to allow early warning or therapeutic intervention, and which allows for continued signal analysis subsequent to the initial detection, and permitting the initial detection to be subsequently confirmed or rejected as a seizure based on the signal data acquired after the initial detection. The present invention addresses limitations associated with existing cardiac-based seizure detection algorithms.

C. SUMMARY

In one respect, disclosed is a method for detecting a seizure event, the method comprising receiving heart beat data versus time for a patient, detecting an increase in the heart rate of a patient from a baseline heart rate to an elevated heart rate, detecting a decrease in heart rate from the elevated heart rate, for a time interval occurring during said decrease in heart rate, determining at least one of a) a rate of decrease in heart rate and b) a rate of change in a rate of decrease in heart rate, and detecting a seizure event in response to determining at least one of a) a rate of decrease in heart rate greater than a threshold rate of decrease, and b) a rate of change in the rate of decrease less than a threshold rate of change in a rate of decrease.

In another respect, disclosed is a system for detecting a seizure event in a patient, the system comprising one or more processors, one or more memory units coupled to the one or more processors, the system being configured to receive data of heart beat versus time, detect an increase in the heart rate from a baseline heart rate to an elevated heart rate, detect a decrease in heart rate from the elevated heart rate, for a time interval occurring during said decrease in heart rate, determine at least one of a) a rate of decrease in heart rate and b) a rate of change in a rate of decrease in heart rate, and detect a seizure event in response to determining at least one of a) that a rate of decrease in heart rate is greater than a threshold rate of decrease, and b) that the rate of change in the rate of decrease is less than a threshold rate of change in a rate of decrease.

In yet another respect, disclosed is a computer program product embodied in a computer-operable medium, the computer program product comprising logic instructions, the logic instructions being effective to process data of heart rate (HR) versus time, and detect an increase in the heart rate of a patient from a baseline heart rate to an elevated heart rate, detect a decrease in heart rate from the elevated heart rate, for a time interval occurring during said decrease in heart rate, determine at least one of a) a rate of decrease in heart rate and b) a rate of change in a rate of decrease in heart rate, and detect a seizure event in response to determining at least one of a) a rate of decrease in heart rate greater than a threshold rate of decrease, and b) a rate of change in the rate of decrease less than a threshold rate of change in a rate of decrease.

In yet another respect, disclosed is a method for detecting a seizure event, the method comprising receiving heart beat data versus time for a patient, determining at least one of a) a rate of decrease in heart rate and b) a rate of change in a rate of decrease in heart rate, and detecting a seizure event in response to determining at least one of a) a rate of decrease in heart rate greater than a threshold rate of decrease, and b) a rate of change in the rate of decrease less than a threshold rate of change in a rate of decrease.

In yet another respect, disclosed is a method for detecting a seizure event, the method comprising receiving heart beat data versus time for a patient, detecting an increase in the heart rate of the patient from a baseline heart rate to an elevated heart rate, detecting a decrease in heart rate from the elevated rate to a first intermediate rate between the elevated rate and the baseline rate, and further detecting a decrease in heart rate to a second intermediate rate between the first intermediate rate and the baseline rate, determining at least one of a) a rate of decrease from said first intermediate rate to said second intermediate rate and b), a rate of change in a rate of decrease in heart rate from said first intermediate rate to said second intermediate rate, and detecting a seizure event in response to determining at least one of a) that the rate of decrease of heart rate from said first intermediate rate to said second intermediate rate is greater than a threshold rate of decrease and b) the rate of change in the rate of decrease from said first intermediate rate to said second intermediate rate is less than a threshold rate of change in a rate of decrease.

Numerous additional embodiments are also possible.

D. BRIEF DESCRIPTION OF THE DRAWINGS

Other objects and advantages of the present disclosure may become apparent upon reading the detailed description and upon reference to the accompanying drawings.

FIG. 7 is a graph of heart rate versus time during an event such as a seizure that causes an increase from a baseline heart rate to an elevated heart rate followed by a decrease in the heart rate back toward the baseline heart rate, in accordance with some embodiments.

Figure 1:
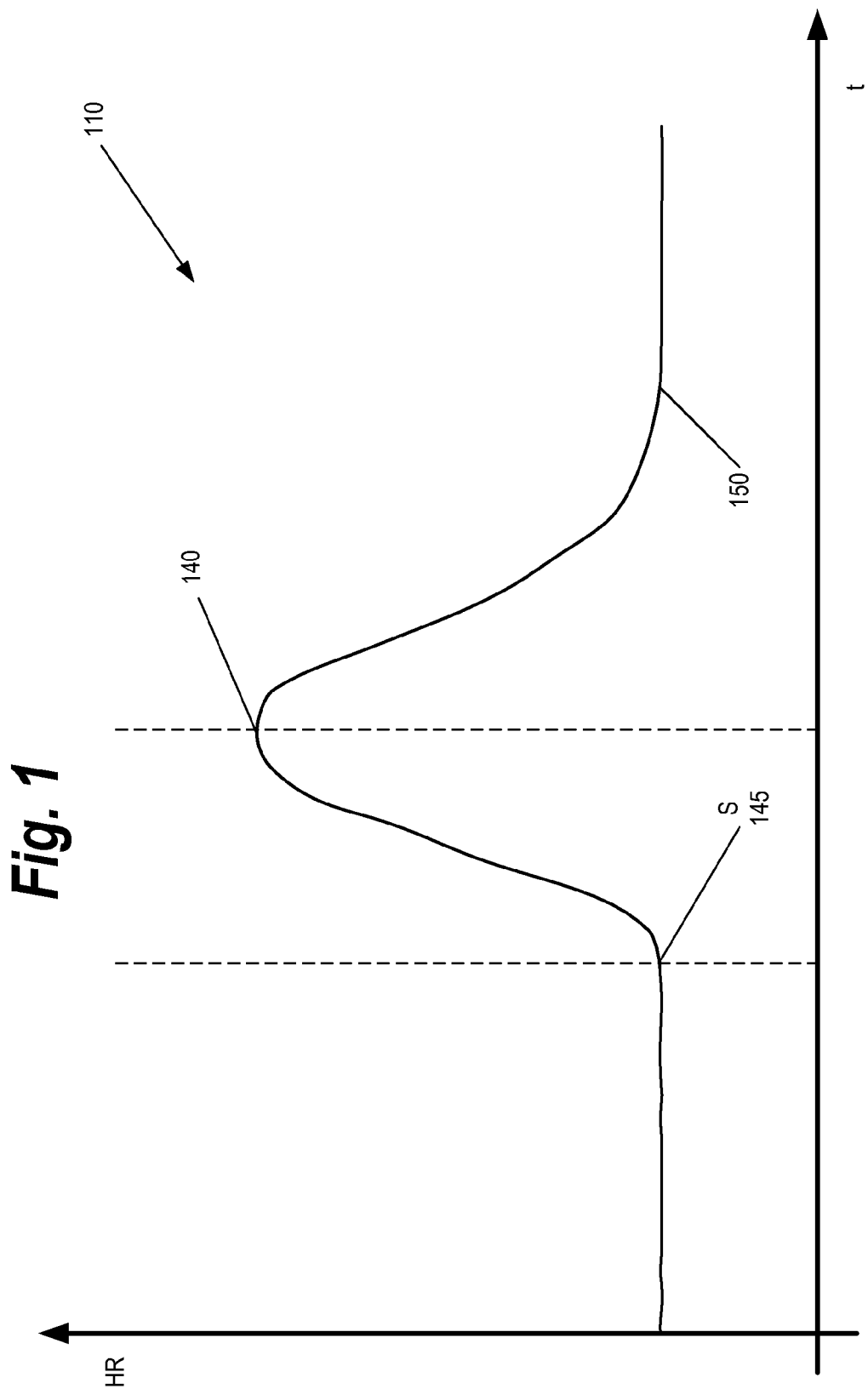
FIG. 1 is a graph illustrating an example of heart rate versus time during a seizure, in accordance with some embodiments.

While the present disclosure is subject to various modifications and alternative forms, specific embodiments of the claimed subject matter are shown by way of example in the drawings and the accompanying detailed description. The drawings and detailed description are not intended to limit the presently claimed subject matter to the particular embodiments. This disclosure is instead intended to cover all modifications, equivalents, and alternatives falling within the scope of the presently claimed subject matter.

E. DETAILED DESCRIPTION

One or more embodiments of the present claimed subject matter are described below. It should be noted that these and any other embodiments are exemplary and are intended to be illustrative of the claimed subject matter rather than limiting. While the present claimed subject matter is widely applicable to different types of systems, it is impossible to include all of the possible embodiments and contexts of the present claimed subject matter in this disclosure. Upon reading this disclosure, many alternative embodiments of the presently claimed subject matter will be apparent to persons of ordinary skill in the art.

The various illustrative logical blocks, modules, circuits, and algorithm steps described in connection with the embodiments disclosed here may be implemented as electronic/computer hardware, computer software, or combinations of the two. Various illustrative components, blocks, modules, circuits, and steps are described generally in terms of their functionality. Whether such functionality is implemented as hardware or software, or allocated in varying degrees to hardware and software respectively, may depend upon the particular application and imposed design constraints. The described functionality may be implemented in varying ways for each particular application, but such implementation decisions should not be interpreted as causing a departure from the scope of the presently claimed subject matter.

FIG. 1 is a graph illustrating an example of heart rate versus time during a seizure, in accordance with some embodiments.

Graph 110 shows the rise of a subject's heart rate (HR) from a pre-ictal baseline HR to a peak HR (at point 140) following the onset of a seizure at time S 145. Graph 110 also shows the decrease of a subject's heart rate (HR) from peak HR 140 to a post-ictal baseline HR (at point 150) following the end of a seizure. For some patients, the post-ictal baseline HR may be different from the pre-ictal baseline HR.

Seizures are often characterized by an increase in HR from an initial or baseline HR to an elevated HR, followed by a decrease in HR from the elevated HR back toward the baseline HR. The increase in HR may begin before, at, or shortly after the electrographic or clinical onset of the seizure, and the decrease in HR may begin at the time the seizure ends. The baseline heart rate may be determined as a statistical measure of central tendency of HR during a desired time window, typically a window prior to an increase in HR associated with a seizure or exertional tachycardia. In one nonlimiting example, the baseline HR may be a median, average or similar statistical measure of HR in a 500 second window. In another embodiment, a number-of-beats window may be used instead of a time window. Various forms of weighting may also be employed to determine the baseline HR, such as exponential forgetting.

Figure 2:
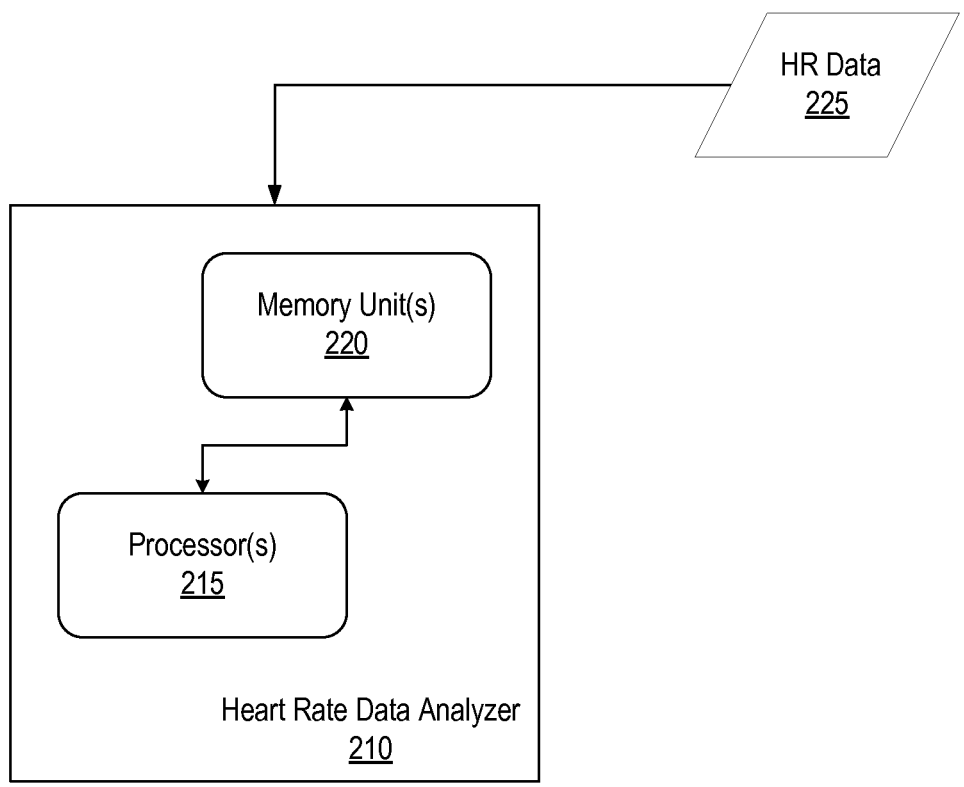
FIG. 2 is a block diagram illustrating a system for detecting a seizure event using heart beat data, in accordance with some embodiments.

FIG. 2 is a block diagram illustrating a system for detecting a seizure event using heart beat data, in accordance with some embodiments.

In some embodiments, heart rate data analyzer 210 is configured to receive and analyze heart rate data 225. Heart rate data 225 may be a series of heart rate values at given points in time. The heart rate data may be received in real time or near real time from a subject or the heart rate data may be data that was previously recorded and is being received from a storage device.

In some embodiments, heart rate data analyzer 210 is configured to analyze the data and identify seizure events that the subject may have suffered and/or is currently suffering. Heart rate data analyzer 210 is additionally configured to distinguish seizure events from nonpathologic events that may have similar effects on a subject's HR. The functionality of heart rate data analyzer 210 may be implemented using one or more processors such as processor(s) 215 and one or more memory units coupled to the one or more processors such as memory unit(s) 220.

Heart rate data analyzer 210 may be configured to identify the offset of a seizure by examining the rate and/or profile with which the HR drops during the offset of the seizure as discussed here.

In some embodiments, systems and methods are disclosed for detecting a seizure event by examining data of the heart rate (HR) versus time of a subject. The subject's heart rate may be obtained in real time or near real time using various methods, including well-known electrocardiogram (ECG) processes. In alternative embodiments, previously stored/recorded HR data may be provided to embodiments of the present invention for analysis.

In some embodiments, heart rate data analyzer 210 may identify a seizure by identifying body signal changes associated with the end of the seizure. Existing seizure detection algorithms focus on identifying the beginning of the seizure (i.e., onset of the ictal state from a non-ictal or pre-ictal state), typically as exemplified by a significant change in a body signal, such as an increase in HR from a baseline HR to an elevated HR. Various attempts to distinguish ictal HR increases from non-ictal increases have been made, but prior art approaches have unacceptably high rates of false positives (i.e., detecting non-ictal changes as a seizure) and false negatives (i.e., failure to detect ictal changes).

In contrast to prior art approaches, the present invention involves identifying a seizure by changes associated with the end of a seizure (i.e., the ictal-to-post-ictal transition). Without being bound by theory, it is believed that changes associated with the end of a seizure may provide improved methods of distinguishing between ictal and non-ictal HR changes.

In some embodiments, a seizure may be identified by determining one or more characteristics of a decrease in HR from an elevated HR back towards a baseline HR. More specifically, an episode of elevated heart rate followed by a return towards a baseline rate may be analyzed and classified as a seizure or as a non-seizure event (for example, exertional tachycardia associated with exercise or normal activity).

In one embodiment, a time interval during a decrease in HR from an elevated HR is analyzed to determine one or more of a) a rate of decrease in HR or b) a rate of change of the rate of decrease in HR. The rate of decrease may be determined from actual data or smoothed data (e.g., by fitting a higher order polynomials to one or more segments of actual data). The rate of decrease may be compared to a threshold rate of decrease associated with a seizure event and/or a threshold rate of decrease associated with a non-seizure event. The rate of change in a rate of decrease may be compared to a threshold rate of change of a rate of decrease associated with a seizure event and/or a threshold rate of change of a rate of decrease associated with a non-seizure event. The event may be detected as a seizure event if the rate of decrease from an elevated heart rate back toward a baseline heart rate exceeds a threshold rate of decrease, or if the rate of change of a rate of decrease is less than a threshold rate of change of a rate of decrease.

In some embodiments, the threshold rate of decrease and/or the threshold rate of change of the rate of decrease may be determined from nonpathologic rates of decrease and/or rates of change of rates of decrease from nonpathologic events that also result in patterns of increasing HR followed by decreasing HR. Such nonpathologic events may include, for example, physical exertion during exercising, climbing or descending stairs, walking, or postural changes. In other embodiments, the threshold rate of decrease and/or the threshold rate of change of the rate of decrease may be determined from seizure events. In some embodiments, different thresholds may be established for different types of seizures, e.g., tonic-clonic seizures, complex partial, simple partial, etc. Thresholds may also be established that are patient-specific, i.e., determined from seizure events of the patient, or from aggregated patient data from multiple patients.

In some embodiments, the rate of decrease in HR (which will be referred to here equivalently as heart beat acceleration, HBA, heart rate drop or HRD), may correspond to an instantaneous or time-interval-specific (e.g., a 15-second moving window) slope of a graph of the HR versus time. This slope may be determined at a specific point(s) and/or for specific intervals during the decrease in HR from an elevated heart rate back towards a baseline heart rate. In one embodiment, the peak heart rate during a tachycardia event (i.e., a heart rate increase above a baseline heart rate followed by a decrease toward the baseline rate) and the baseline rate may be used to determine a peak-to-baseline (PTB) value that is useful for performing calculations according to certain embodiments. For a given point along the decreasing HR curve from the peak heart rate, one useful rate of decrease may be determined as the average slope (or average rate of decrease) from the peak to the given point. In other embodiments, short-term rates of decrease may be established for a short-term time window along the decreasing HR curve from peak to baseline. Short-term rates of decrease may be determined for a 5-second or 5-beat window, for example, or from the last two heart beats.

In certain embodiments, particular short-term rates of decrease may be useful to compare to later short-term rates of decrease. It has been appreciated by the present inventor that PTB decreases in heart rate for seizure events and non-seizure events differ qualitatively. In particular, decreases in HR for seizure events tend to maintain a relatively constant rate of decrease during most of the PTB decline. In non-seizure events, by contrast, rates of decrease tend to decline as the HR approaches the baseline HR. Thus, for seizure events the slope of the PTB heart rate curve tends to be relatively straight. The slope of the PTB heart rate curve for non-seizure tachycardia episodes, on the other hand, tends to flatten as the HR approaches the baseline heart rate, resulting in a HR curve that is "upwardly concave" near the baseline for non-seizure events.

Because the differences in HR decline between seizure and non-seizure events is most prominent near the baseline, in some embodiments, rates of decline and/or rates of change of rates of decline are determined at rates below the rate halfway between the peak and the baseline heart rate.

In some embodiments, a seizure end may be identified in response to determining that the HR drop at a specific point during the PTB transition is greater (in absolute value since during a heart rate decrease the slope is negative) than a seizure threshold value. In some embodiments, HRDs during PTB transitions in healthy subjects for nonpathologic events are smaller than HRDs during a corresponding time during a seizure event. The threshold HRD may accordingly be chosen in order to maximize the accuracy of the seizure identification process. Binary classification statistics may be used to maximize the accuracy of the detection by appropriately balancing the sensitivity and specificity of the identification process.

In some embodiments, the HRD (the slope of the HR v. time graph) at a particular point may be computed numerically from the HR v. time data using well-known numerical computation techniques for calculating slope using numerical data.

In some embodiments, average HRDs may be used over one or more intervals for identifying a seizure offset. Intervals may be chosen anywhere between a peak HR and the return towards a baseline HR, the peak HR being the highest HR value reached during the seizure or nonpathologic event, and the baseline HR being the HR of the subject prior to the tachycardia event under consideration (whether pathological or non-pathological). For example, a First Half HRD may be computed for an interval between the peak HR value and the HR that is halfway between the baseline HR and the peak HR. Similarly, a Middle Half HRD may be computed for an interval between the HR that is 25% of the way between the peak HR and the baseline HR and the HR that is 75% of the way between the peak HR and the baseline HR, and a Second Half HRD may be computed for the interval between the HR that is 50% of the distance from peak-to-baseline, and the baseline HR itself. Similarly, a First Third HRD may be computed between the peak HR and the HR that is ⅓ of the way from the peak HR to the baseline HRD, and a Final Third HRD may be computed between the HR that is ⅔ of the way from the peak HR to the baseline HR and the baseline HR itself. Similar intervals may be constructed, and the HRD computed, depending upon the points in the decline from peak to baseline that provides a desirable level of discrimination between seizure and non-seizure events. More generally, in some embodiments, an average HRD over an interval from point A to point B may be computed by dividing the HR change from point A to point B by the time change from point A to point B.

In some embodiments, the offset of a seizure may be identified in response to determining that the First Half HRD and Middle Half HRD are substantially equal. For example, the offset of the seizure may be identified in response to determining that the First Half HRD and the Middle Half HRD are within a certain percentage of each other. It should be noted that other appropriate intervals/average HRDs may be selected and used in various combinations to identify a seizure.

In some embodiments, a seizure may be identified by comparing HRDs at one or more points and/or by comparing average HRDs over one or more intervals to HRDs threshold values. In some embodiments, the threshold HRD values may be determined by examining typical corresponding values of HRDs for seizure and nonpathologic events. For example, a seizure may be identified in response to determining that an average One Third HRD is above a certain threshold, which is determined by examining corresponding One Third HRD values for typical seizures as well as nonpathologic events.

In some embodiments, a general profile of the HR versus time during a seizure offset may be determined and compared to known HR versus time profiles during seizures and nonpathologic events. In some embodiments, a seizure offset may be identified in response to determining that there exists a substantial match between the determined profile and the known seizure profiles, or a substantial dissimilarity between the determined profile and one or more known nonpathologic profiles. In some embodiments, a seizure may be identified in response to determining that a seizure profile is substantially similar to a linear seizure profile and substantially dissimilar to a nonpathologic profile such as an asymptotically decreasing profile (for example, a decreasing exponential profile), a concave decreasing profile, etc.

Figure 3:
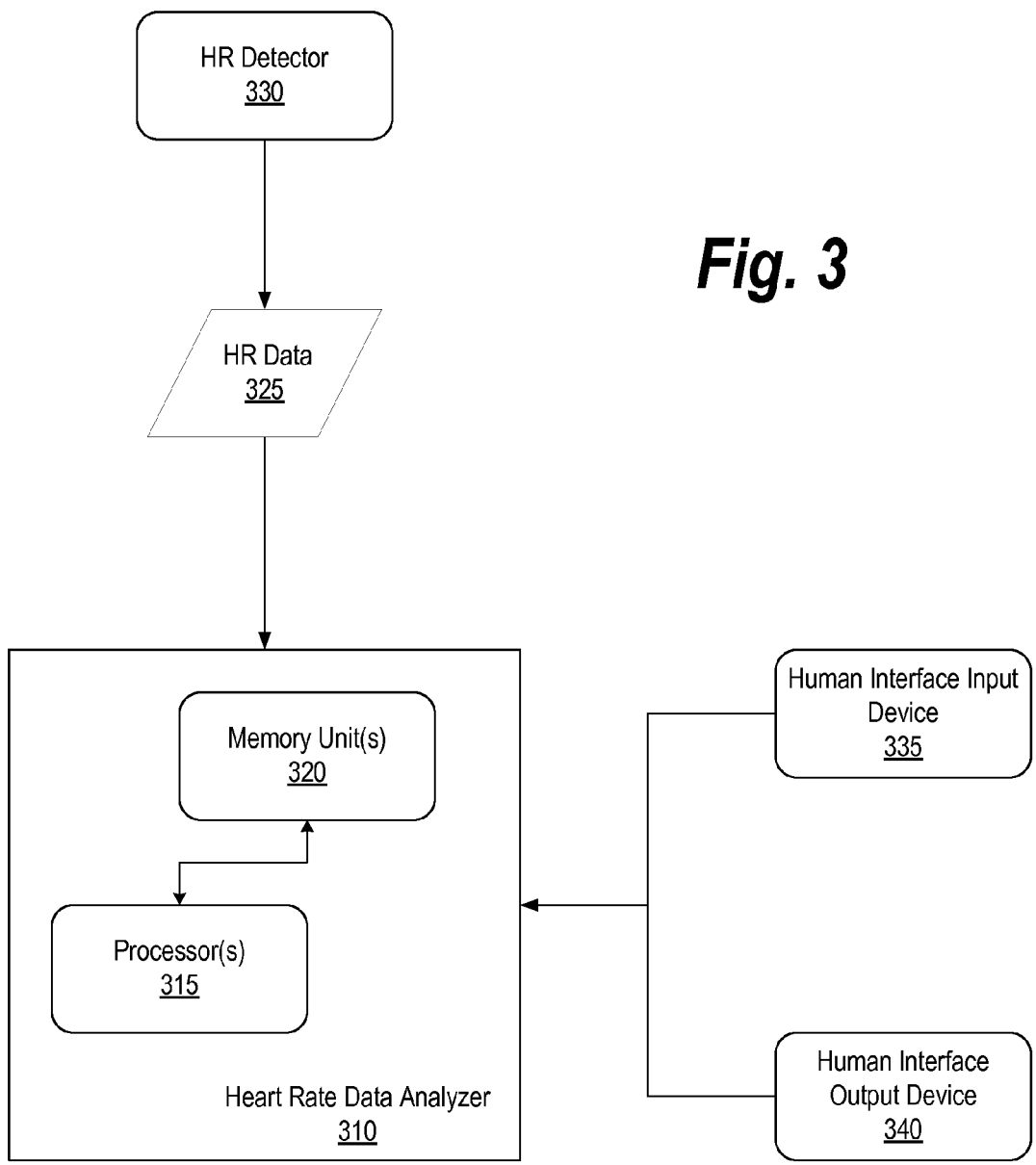
FIG. 3 is a block diagram illustrating an alternative system for detecting a seizure event using heart beat data, in accordance with some embodiments.

FIG. 3 is a block diagram illustrating an alternative system for detecting a seizure event using heart beat data, in accordance with some embodiments.

In some embodiments, heart rate data analyzer 310 is configured to receive and analyze heart rate data 325. Heart rate data 325 may be a series of heart rate values at given points in time. The heart rate data may be received in real time or near real time from heart rate detection equipment connected to a subject, such as HR detector 330. HR detector 330, in some embodiments may comprise electrocardiogram equipment, which is configured to couple to a subject's body in order to detect the subject's heart beat.

In some embodiments, heart rate data analyzer 310 is configured to analyze the data and identify seizure events that the subject may have suffered and/or is currently suffering. The functionality of heart rate data analyzer 310 may be implemented using one or more processors such as processor(s) 315 and one or more memory units coupled to the one or more processors such as memory unit(s) 320.

Heart rate data analyzer 310 may be configured to identify the offset of a seizure by examining the rate and generally the profile with which the HR drops during the offset of the seizure as discussed here.

Heart rate data analyzer 310 may also be coupled to human interface input device 335 and human interface output device 340. Human interface input device 335 may be configured to provide a user of the system a means with which to input data into the system and with which to generally control various options. Accordingly, human interface input device 335 may be at least one of a computer keyboard, a touch screen, a microphone, a video camera, etc.

Human interface output device 340 may be configured to provide information to a user of the system visually, audibly, etc. Accordingly, human interface output device 340 may be at least one of a computer display, one or more audio speakers, haptic feedback device, etc. In some embodiments, human interface input device 335 and human interface output device may be combined into a single unit.

Figure 4:
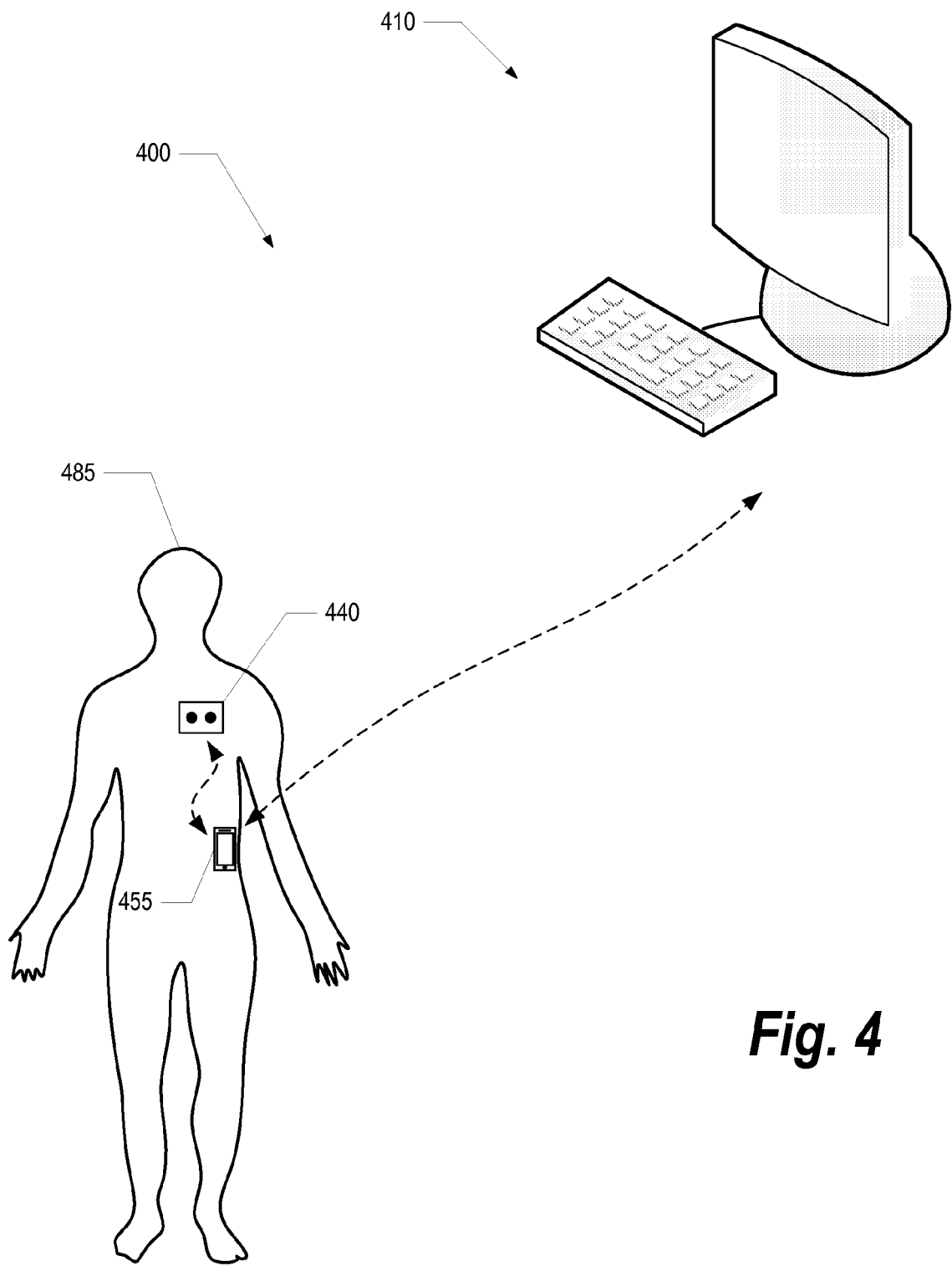
FIG. 4 is a diagram illustrating an example of obtaining heart beat data from a subject using electrocardiogram equipment, in accordance with some embodiments.

FIG. 4 is a diagram illustrating an example of obtaining heart beat data from a subject using electrocardiogram equipment, in accordance with some embodiments.

A particular embodiment of a system for monitoring heart beat data from a subject is shown in the Figure and generally designated 400. System 400 may include, a heart beat sensor 440, a controller 455, and a computer 410.

In some embodiments, heart beat and/or heart rate data may be collected by using an external or implanted heart beat sensor and related electronics (such as heart beat sensor 440), and a controller that may be wirelessly (or via wire) coupled to the sensor for detecting seizure events based upon the patient's heart signal, such as controller 455. In one embodiment, sensor 440 may comprise electrodes in an externally worn patch adhesively applied to a skin surface of patient 485. In some embodiments, sensor 440 may be implanted under the patient's skin. The patch may include electronics for sensing and determining a heart beat signal (e.g., an ECG signal), such as an electrode, an amplifier and associated filters for processing the raw heart beat signal, an A/D converter, a digital signal processor, and in some embodiments, an RF transceiver wirelessly coupled to a separate controller unit, such as controller 455. In some embodiments, the controller unit may be part of the patch electronics.

The controller 455 may implement an algorithm for detection of seizure events based on the heart signal. It may comprise electronics and memory for performing computations of, e.g. HR parameters such as median HR values for the first and second windows, determination of ratios and/or differences of the first and second HR measures, and determination of seizure onset and offset times according to the foregoing disclosure. In some embodiments, the controller 455 may include a display and an input/output device. The controller 455 may comprise part of a handheld computer such as a PDA or smartphone, a cellphone, an iPod® or iPad®, etc.

In the example shown, sensor 440 may be placed on a body surface suitable for detection of heart signals. Electrical signals from the sensing electrodes may be then fed into patch electronics for filtering, amplification and A/D conversion and other preprocessing, and creation of a time-of-beat sequence (e.g., an R-R interval data stream), which may then be transmitted to controller 455. Sensor 440 may be configured to perform various types of processing to the heart rate data, including filtering, determination of R-wave peaks, calculation of R-R intervals, etc. In some embodiments, the patch electronics may include the functions of controller 455, illustrated in FIG. 4 as separate from sesnor 440.

The time-of-beat sequence may be then provided to controller 455 for processing and determination of seizure onset and offset times and related seizure metrics. Controller 455 may be configured to communicate with computer 410. Computer 410 may be located in the same location or computer 410 may be located in a remote location from controller 455. Computer 410 may be configured to further analyze the heart data, store the data, retransmit the data, etc. Computer 410 may comprise a display for displaying information and results to one or more users as well as an input device from which input may be received by the one or more users. In some embodiments, controller 455 may be configured to perform various tasks such as calculating first and second HR measures, HR parameters, comparing HR parameters to appropriate thresholds, and determining of seizure onset and seizure end times, and other seizure metrics.

Figure 5:
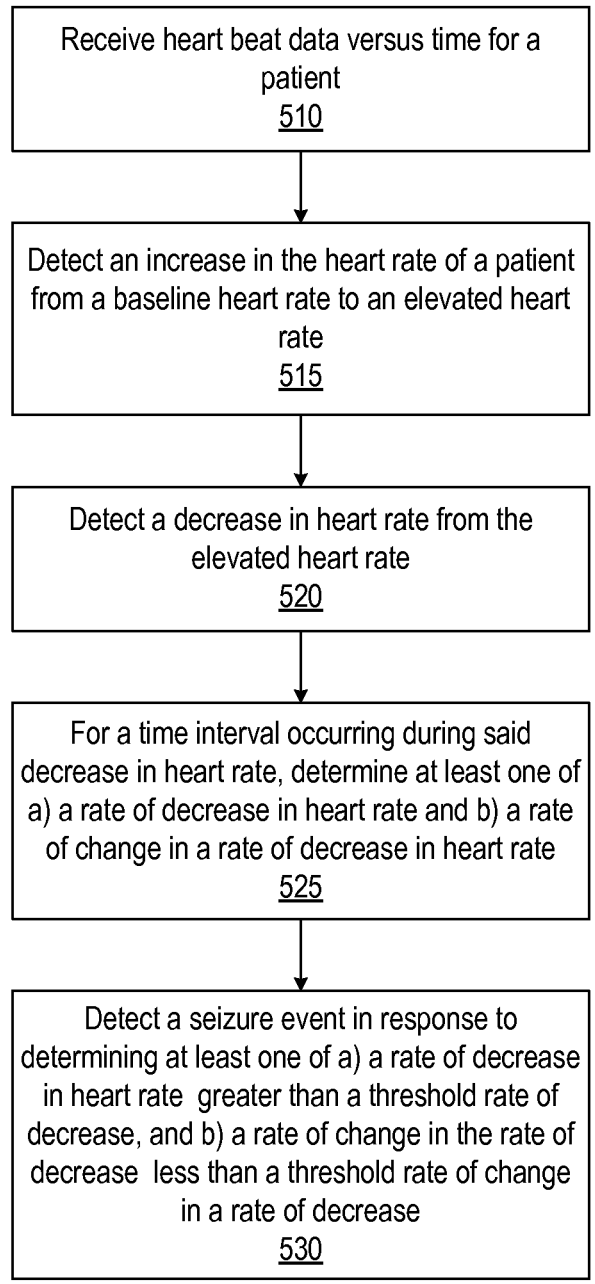
FIG. 5 is a flow diagram illustrating a method for detecting a seizure event using heart beat data, in accordance with some embodiments.

FIG. 5 is a flow diagram illustrating a method for detecting a seizure event using heart beat data, in accordance with some embodiments.

In some embodiments, the method illustrated in this figure may be performed by one or more of the systems illustrated in FIG. 2, FIG. 3, and FIG. 4.

At block 510, heart beat data versus time for a patient is received.

At block 515, an increase in the heart rate of a patient is detected from a baseline heart rate to an elevated heart rate.

At block 520, a decrease in heart rate is detected from the elevated heart rate.

At block 525, for a time interval occurring during said decrease in heart rate, at least one of a) a rate of decrease in heart rate and b) a rate of change in a rate of decrease in heart rate, is determined.

At block 530, a seizure event is detected in response to determining at least one of a) a rate of decrease in heart rate greater than a threshold rate of decrease, and b) a rate of change in the rate of decrease less than a threshold rate of change in a rate of decrease. In some embodiments, detecting of the seizure event comprises determining the end of a seizure event. The threshold rate of decrease or threshold rate of change of rate of decrease may in some embodiments be selected after examining previous such rates for seizures as well as nonpathologic events.

Figure 6:
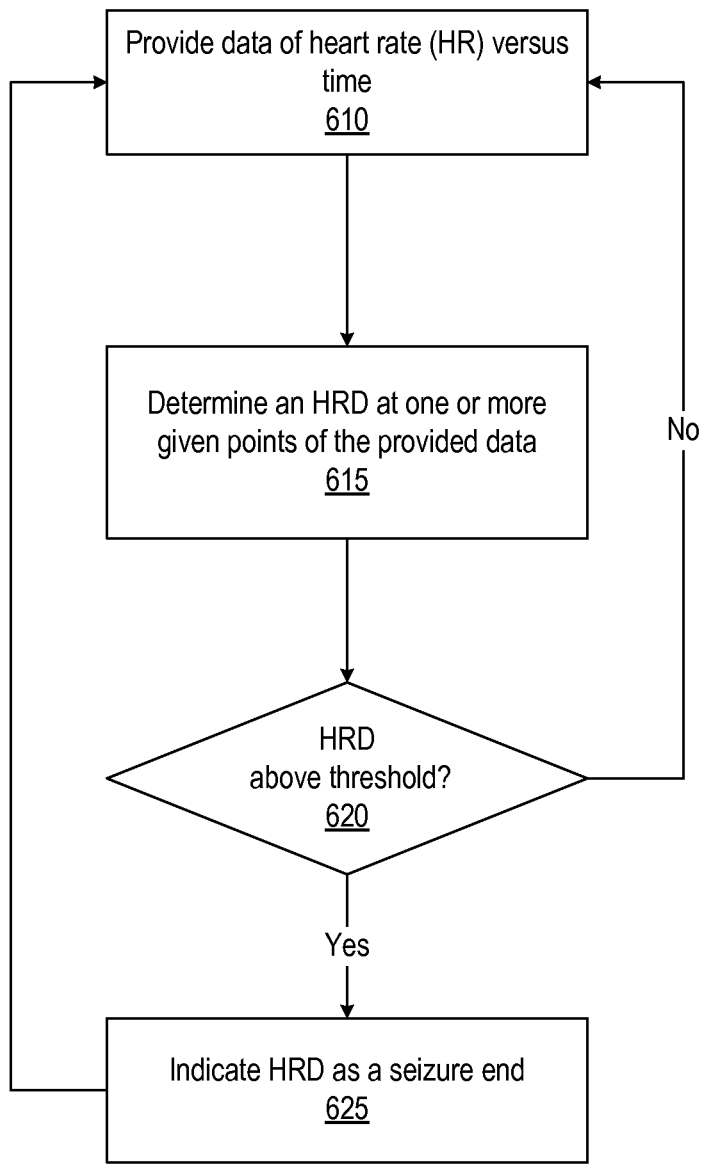
FIG. 6 is a flow diagram illustrating an alternative method for detecting a seizure event using heart rate data, in accordance with some embodiments.

FIG. 6 is a flow diagram illustrating an alternative method for detecting a seizure event using heart rate data, in accordance with some embodiments.

In some embodiments, the method illustrated in this figure may be performed by one or more of the systems illustrated in FIG. 2, FIG. 3, and FIG. 4.

At block 610, data of heart rate (HR) versus time is provided. In some embodiments, the data may be provided in real time or near real time or the data may be retrieved from storage.

At block 615, an HR drop rate or HRD (which corresponds to a slope of the HR versus time data) is determined at one or more points of the provided data. In some embodiments, instead of an HRD at a single point, an average HRD may be determined over an interval of the HRD versus time data/graph.

At decision 620, a determination is made as to whether the HRD is above a threshold HRD. In some embodiments, the threshold HRD may be chosen by examining previous seizure and nonpathologic HRDs.

If the HRD is not above the threshold HRD, decision 620 branches to the "no" branch, and processing returns to block 610 where additional data is received for processing. On the other hand, if the HRD is above the threshold HRD, decision 620 branches to the "yes" branch, and processing continues at block 625.

At block 625, the examined HRD is indicated as indicative of the end of a seizure, and thus a seizure event is identified. Subsequently, processing returns to block 610 where additional data is provided for processing.

FIG. 7 is a graph of heart rate versus time during an event such as a seizure that causes an increase from a baseline heart rate to an elevated heart rate followed by a decrease in the heart rate back toward the baseline heart rate, in accordance with some embodiments.

Graph 710 shows the rise of a subject's heart rate (HR) from a baseline HR to a peak HR and then the fall of the HR back toward the baseline HR after some time for a typical seizure case and for a non-pathological case. Point ½ HR marks the HR value between the peak HR and the baseline HR, and point ¾ HR marks the HR value that is ¾ of the way from the peak HR to the baseline HR. In the figure, the non-pathological HR drop is indicated by the dotted line.

In some embodiments, in order to determine whether the fall in the HR corresponds to the end of a seizure, the slope of the graph (i.e., HRD) may be computed. In some embodiments, the instantaneous slope may be computed at a point. In alternative embodiments, an average slope may be computed between two points.

For example, the instantaneous slope may be computed at point 725 and corresponding point 730 for the non-pathological case. The two slopes for the typical seizure case and the non-pathological case are illustrated by dashed lines 727 and 732 respectively.

Alternatively, an average slope may be computed between points 725 and 726 and between corresponding points 730 and 731 for the non-pathological case. The two average slopes for the typical seizure case and the non-pathological case are illustrated by dashed lines 728 and 733 respectively.

Regardless of the method used to compute the slope, a seizure may be identified in response to determining that the slope is below (or above in absolute value) a certain threshold value. As seen by the figure, typical seizure cases exhibit slopes that are smaller (or larger in absolute value) when compared to non-pathological cases as indicated by dashed lines representing these slopes.

In alternative embodiments, a seizure may be identified in response to determining that the average HRDs in two intervals is substantially equal. For example, the average HRD may be computed and compared for two intervals by dividing the difference in HR by the difference in time at the beginning and end of the intervals. Then, as discussed here, the seizure is identified in response to determining that the HRDs for the two intervals are substantially equal, or differ by only a threshold slope difference. By comparison, a typical non-pathological case will exhibit a greater difference in the average slope between two different intervals.

Similarly, the concavity of the graph may be computed for a certain interval and compared to certain threshold concavities. As can be seen by the figure, typical seizure cases exhibit concavities that are typically larger compared to the concavities of non-pathological events. In some embodiments, the concavity may be computed by determining the second time derivative of the HR. Thus, a seizure may be identified in response to determining that the concavity (average or at a given point) is higher than a threshold concavity value.

The previous description of the disclosed embodiments is provided to enable any person skilled in the art to make or use the present claimed subject matter. Various modifications to these embodiments will be readily apparent to those skilled in the art, and the generic principles defined herein may be applied to other embodiments without departing from the spirit or scope of the claimed subject matter. Thus, the present claimed subject matter is not intended to be limited to the embodiments shown herein but is to be accorded the widest scope consistent with the principles and novel features disclosed here.

The benefits and advantages that may be provided by the present claimed subject matter have been described above with regard to specific embodiments. These benefits and advantages, and any elements or limitations that may cause them to occur or to become more pronounced are not to be construed as critical, required, or essential features of any or all of the claims. As used here, the terms "comprises," "comprising," or any other variations thereof, are intended to be interpreted as non-exclusively including the elements or limitations which follow those terms. Accordingly, a system, method, or other embodiment that comprises a set of elements is not limited to only those elements and may include other elements not expressly listed or inherent to the claimed embodiment.

While the present claimed subject matter has been described with reference to particular embodiments, it should be understood that the embodiments are illustrative and that the scope of the claimed subject matter is not limited to these embodiments. Many variations, modifications, additions and improvements to the embodiments described above are possible. It is contemplated that these variations, modifications, additions and improvements fall within the scope of the present disclosure as detailed within the following claims.

What is claimed is:

1. A method for detecting a seizure event, the method comprising:
   receiving heart beat data versus time for a patient;
   detecting an increase in a heart rate of the patient based on the heart rate data from a baseline heart rate to an elevated heart rate;
   detecting a decrease in heart rate from the elevated heart rate;
   for a time interval occurring during said decrease in heart rate, determining at least one of a) a rate of change of the decrease in heart rate and b) a rate of change in a rate of decrease in heart rate; and
   determining occurrence of a seizure event in response to the rate of change of the decrease in heart rate satisfying a threshold rate.

2. The method of claim 1, wherein the rate of change of the decrease in heart rate at the time satifies the threshold rate when the rate of change of the decrease in heart rate at the time is greater than the threshold rate, and wherein the threshold rate in based on a non-seizure event.

3. The method of claim 1, further comprising:
   determining a rate of change of the rate of change of the decrease in her heart rate at the time; and
   confirming the occurrence of the seizure event when the rate of change of the rate of change of the decrease in heart rate at the time satisfies a second threshold.

4. The method of claim 3, wherein the second threshold is satisfied when the rate of change in the rate of change of the decrease in heart rate at the time is greater than the second threshold, and wherein the second threshold is based on a non-pathological event.

5. The method of claim 1, further comprising:
   determining an initial detection of a seizure event based upon the increase in heart rate;
   determining a profile of the decrease in heart rate;
   comparing the profile of the decrease in heart rate to a known profile of a seizure event decrease in heart rate; and
   confirming the occurrence of the seizure event in response to determining that the profile of the decrease in heart rate is substantially similar to the known profile of the seizure event decrease in heart rate.

6. The method of claim 1, further comprising:
   determining a profile of the rate of change of decrease in heart rate;
   comparing the profile of the rate of change of decrease in heart rate to a known profile of a nonpathologic rate of change of decrease in heart rate; and
   confirming the detection of the seizure event in response to determining that the profile of the rate of change of decrease in heart rate is substantially dissimilar to the known profile of the nonpathologic rate of change of decrease in heart rate.

7. The method of claim 6, wherein the known profile of the nonpathologic rate of change of decrease in heart rate is at least one of: an asymptotically decreasing profile, an exponentially decreasing profile, or a concave decreasing profile.

8. The method of claim 1, further comprising:
   determining a first average rate of change of heart rate over a first time interval;
   determining a second average rate of change of heart rate over a second time interval, wherein the second time interval is different from the first time interval; and
   confirming the occurrence of the seizure event in response to determining that the first average rate of change of heart rate is substantially equal to the second average rate of change of heart rate.

9. The method of claim 1, wherein the elevated heart rate is a particular rate of at least one of 10 beats per minute greater than the baseline heart rate or 10 percent greater than the baseline heart rate.

10. A system for detecting a seizure event in a patient, the system comprising:
    one or more processors; and
    one or more memory units coupled to the one or more processors;
    the one or more processors configured to:
    receive data of heart beat versus time for a patient;
    detect an increase in a heart rate from a baseline heart rate to an elevated heart rate;
    detect a decrease in heart rate from the elevated heart rate for a time interval occurring during said decrease in heart rate,
    determine a first average rate of change of decrease in heart rate over a first time interval;
    determine a second average rate of change of decrease in heart rate over a second time interval, wherein the second time interval is different from the first time interval; and
    indicate occurrence of detect a seizure event in response to determining at least one of a) that a rate of decrease in heart rate is greater than a threshold rate of decrease, and b) that the rate of change in the rate of decrease is less than a threshold rate of change in a rate of decrease the first average rate of change of decrease in heart rate being within a particular percentage of the second average rate of change of decrease in heart rate.

11. The system of claim 10, wherein the one or more processors are further comprising to:
    determine a rate of change in heart rate at a particular time; and confirm the occurrence of the seizure event when the rate of change in heart rate at the particular time satifies a threshold, comprising a first intermediate heart rate and a second intermediate heart rate, wherein said first intermediate heart rate is a heart rate between said elevated heart rate and said baseline heart rate and occurring during said decrease in heart rate from the elevated heart rate, and wherein said second intermediate heart rate is a heart rate between said first intermediate heart rate and said baseline heart rate and occurring during said decrease in heart rate from the elevated heart rate, wherein the system being configured to identify the seizure event comprises the system being configured to detect the seizure event in response to determining at least one of a) that a rate of decrease in heart rate from said first intermediate heart rate to said second intermediate heart rate is greater than a threshold rate of decrease, and b) that a rate of change in a rate of decrease in heart rate from first intermediate heart rate to said second intermediate heart rate is less than a threshold rate of change in a rate of decrease.

12. The system of claim 10, where the one or more processors are further configured to:
determine a profile of the decrease in heart rate;
compare the profile of the decrease in heart rate to a known profile of a nonpathological decrease in heart rate; and
confirm the occurrence of the seizure event in response to determining that the profile of the decrease in heart rate is substantially dissimilar to the known profile.

13. The system of claim 10, where the one or more processors are further configured to:
determine a profile of the decrease in heart rate;
compare the profile of the decrease in heart rate to a known profile of a seizure event decrease in heart rate; and
confirm the occurrence of the seizure event in response to determining that the profile of the decrease in heart rate is substantially similar to the known profile of the seizure event decrease in heart rate.

14. The system of claim 13, wherein the known profile of the seizure event decrease in heart rate is substantially a linearly decreasing profile.

15. The system of claim 10, where the one or more processors are further configured to:
determine a rate of change in a rate of a rate of change in heart rate at a particular time; and
confirm the occurrence of the seizure event when the rate of change in the rate of change in heart rate at the particular time satisfies a second threshold,
determine a first average decreasing heart rate over a first interval occurring during said decrease in heart rate;
determine a second average decreasing heart rate over a second interval occurring during said decrease in heart rate, wherein the second interval is different from the first interval; and
confirm the detection of the seizure event in response to determining that the first average decreasing heart rate is substantially equal to the second average decreasing heart rate.

16. A computer program product embodied in a computer-operable medium, the computer program product comprising logic instructions, the logic instructions executable to:
process data of heart rate versus time for a patient to detect an increase in the heart rate of the patient from a baseline heart rate to an elevated heart rate;
detect a decrease in heart rate from the elevated heart rate;
for a time interval occurring during said decrease in heart rate, determine at least one of a) a rate of decrease in heart rate and b) a rate of change in a rate of decrease in heart rate; and
indicate occurrence of a seizure event in response to determining the rate of change in the rate of decrease satisfies a threshold.

17. The product of claim 16, the logic instructions being further executable to:
determine a first average heart rate over a first time interval;
determine a second average heart rate over a second time interval, wherein the second time interval is different from the first time interval; and
receive heart beat data versus time for a patient;
detect an increase in the heart rate of the patient from a baseline heart rate to an elevated heart rate;
detect a decrease in heart rate from the elevated rate to a first intermediate rate between the elevated rate and the baseline rate, and further
detecting a decrease in heart rate to a second intermediate rate between the first intermediate rate and the baseline rate;
determine at least one of a) a rate of decrease from said first intermediate rate to said second intermediate rate and b) a rate of change in a rate of decrease in heart rate from said first intermediate rate to said second intermediate rate; and
confirm the occurrence of the seizure event in response to the first average heart rate being within a particular perecentage of the second average heart rate.

18. The product of claim 16, wherein the elevated heart rate is a rate at least a specified threshold above the baseline heart rate.

19. The product of claim 16, wherein the threshold is satisfied when the rate of change in the rate of decrease is less than the threshold, and wherein the threshold is based on a non-seizure event.

20. The product of claim 16, wherein the baseline heart rate is determined as a statistical measure of central tendency of heart rate during a time window,
detect a seizure event based on an increase in heart rate from a baseline heart rate to an intermediate elevated heart rate between the elevated heart rate and the baseline heart rate; and
detect a seizure event in response to determining at least one of that the rate of decrease of heart rate from said first intermediate rate to said second intermediate rate is greater than a threshold rate of decrease and the rate of change in the rate of decrease from said first intermediate rate to said second intermediate rate is less than a threshold rate of change in a rate of decrease comprises confirming said detecting a seizure event based on an increase in heart rate.

* * * * *